United States Patent
Chandran

(10) Patent No.: US 12,400,741 B2
(45) Date of Patent: Aug. 26, 2025

(54) SELECTIVE EXTRACTION OF LATE EXPONENTIALS

(71) Applicant: Howard University, Washington, DC (US)

(72) Inventor: Preethi Lourdes Chandran, Washington, DC (US)

(*) Notice: Subject to any disclaimer, the term of this patent is extended or adjusted under 35 U.S.C. 154(b) by 940 days.

(21) Appl. No.: 17/188,970

(22) Filed: Mar. 1, 2021

(65) Prior Publication Data

US 2021/0272656 A1    Sep. 2, 2021

Related U.S. Application Data

(60) Provisional application No. 62/983,137, filed on Feb. 28, 2020.

(51) Int. Cl.
*G16C 20/20* (2019.01)

(52) U.S. Cl.
CPC .................................. *G16C 20/20* (2019.02)

(58) Field of Classification Search
CPC .................................................. G16C 20/20
See application file for complete search history.

(56) References Cited

U.S. PATENT DOCUMENTS

| | | | | |
|---|---|---|---|---|
| 6,675,106 B1* | 1/2004 | Keenan | ...................... | G01J 3/28 702/194 |
| 2003/0219820 A1* | 11/2003 | Epps | .................... | G01N 33/542 435/7.1 |
| 2006/0176479 A1* | 8/2006 | Laurence | .............. | G01J 3/4406 250/458.1 |
| 2007/0109536 A1* | 5/2007 | Weiss | .................... | G01J 3/4338 356/318 |
| 2014/0152978 A1* | 6/2014 | Carr | ....................... | G01N 15/14 356/73 |
| 2018/0070830 A1* | 3/2018 | Sutin | ....................... | A61B 5/72 |
| 2019/0072472 A1* | 3/2019 | Clayton | ............. | G01N 15/0227 |
| 2020/0348234 A1* | 11/2020 | Hendrix | ............. | G01N 21/6428 |

OTHER PUBLICATIONS

Scotti et al., The Contin algorithm, J. Chem. Phys. 142, 2015 (Year: 2015).*
Stetefeld et al., Dynamic light scattering, IUPAB, 2016 (Year: 2016).*
Russo, A Practical Minicourse in Dynamic Light Scattering, LSU, 2012 (Year: 2012).*
Patil et al., Comparison of NMR and Dynamic Light Scattering, AAPS, 2017 (Year: 2017).*
Benda et al., Fluorescence spectral correlation spectroscopy, Optical Society of America, 2014 (Year: 2014).*
Kapusta et al., Fluorescence Lifetime Correlation Spectroscopy, Int. J. Mol. Sci. 2012 (Year: 2012).*
Felekyan et al., Filtered FCS, SPIE, 2009 (Year: 2009).*

* cited by examiner

*Primary Examiner* — Kyle R Quigley
(74) *Attorney, Agent, or Firm* — Sughrue Mion, PLLC

(57) ABSTRACT

A method, computer program, and computer system is provided for analyzing chemical mixtures. Data corresponding to a mixture comprising one or more component species is obtained. A parameter corresponding to a species having a largest parameter value within the mixture is determined from among the component species. The parameter associated with the species having the largest parameter value is subtracted from the data. One or more remaining species associated with the mixture are detected.

17 Claims, 6 Drawing Sheets

SELECTIVE EXTRACTION OF LATE EXPONENTIALS

BACKGROUND

This disclosure relates generally to field of data processing, and more particularly to chemical mixture analysis.

Techniques such as Dynamic Light Scattering (DLS) and Fluorescence Correlation Spectroscopy (FCS) track the time-scale dependence of the similarities or auto-correlation in the light and fluorescent signal reaching a detector. In the case of DLS, the pathway of light is intercepted by a solution of particles smaller than its wavelength and get scattered in all directions. Photodetectors may be positioned at angles away from the path of the incoming light to measure light scattered in such a direction. The scattered light in any direction depends both on the scattering properties of particles as well as their relative arrangement, which causes constructive or destructive interference between the light scattered by the particles. As particles move and the arrangement changes, the intensity of light reaching the detector changes.

SUMMARY

Embodiments relate to a method, system, and computer readable medium for mixture analysis. According to one aspect, a method for mixture analysis is provided. The method may include obtaining data corresponding to a mixture comprising one or more component species. A parameter corresponding to a species having a largest parameter value within the mixture is determined from among the component species. The parameter associated with the species having the largest parameter value is subtracted from the data. One or more remaining species associated with the mixture are detected.

According to another aspect, a computer system for mixture analysis is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include obtaining data corresponding to a mixture comprising one or more component species. A parameter corresponding to a species having a largest parameter value within the mixture is determined from among the component species. The parameter associated with the species having the largest parameter value is subtracted from the data. One or more remaining species associated with the mixture are detected.

According to yet another aspect, a computer readable medium for mixture analysis is provided. The computer readable medium may include one or more computer-readable storage devices and program instructions stored on at least one of the one or more tangible storage devices, the program instructions executable by a processor. The program instructions are executable by a processor for performing a method that may accordingly include obtaining data corresponding to a mixture comprising one or more component species. A parameter corresponding to a species having a largest parameter value within the mixture is determined from among the component species. The parameter associated with the species having the largest parameter value is subtracted from the data. One or more remaining species associated with the mixture are detected.

BRIEF DESCRIPTION OF THE DRAWINGS

These and other objects, features and advantages will become apparent from the following detailed description of illustrative embodiments, which is to be read in connection with the accompanying drawings. The various features of the drawings are not to scale as the illustrations are for clarity in facilitating the understanding of one skilled in the art in conjunction with the detailed description. In the drawings.

DETAILED DESCRIPTION

Figure 1:
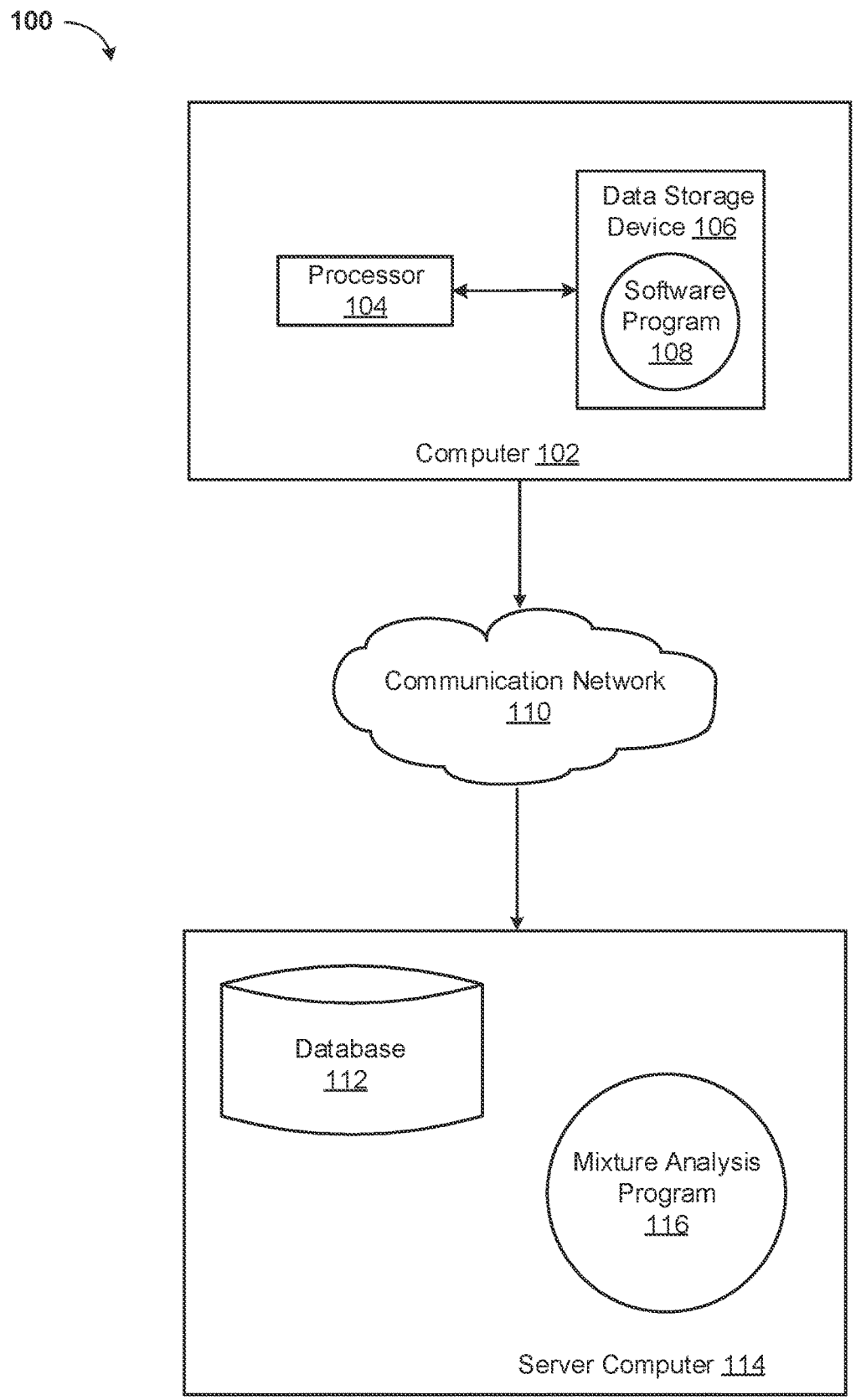
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. Those structures and methods may, however, be embodied in many different forms and should not be construed as limited to the exemplary embodiments set forth herein. Rather, these exemplary embodiments are provided so that this disclosure will be thorough and complete and will fully convey the scope to those skilled in the art. In the description, details of well-known features and techniques may be omitted to avoid unnecessarily obscuring the presented embodiments.

Embodiments relate generally to the field of data processing, and more particularly to chemical mixture analysis. The following described exemplary embodiments provide a system, method and computer program to, among other things, analyze chemical mixtures. Therefore, some embodiments have the capacity to improve the field of computing by allowing for analysis of chemical mixtures at steady state based on iteratively subtracting data corresponding to the largest component of a mixture.

As previously described, techniques such as Dynamic Light Scattering (DLS) and Fluorescence Correlation Spectroscopy (FCS) track the time-scale dependence of the similarities or auto-correlation in the light and fluorescent signal reaching a detector. In the case of DLS, the pathway of light is intercepted by a solution of particles smaller than its wavelength and get scattered in all directions. Photodetectors may be positioned at angles away from the path of the incoming light to measure light scattered in such a direction. The scattered light in any direction depends both on the scattering properties of particles as well as their relative arrangement, which causes constructive or destructive interference between the light scattered by the particles.

As particles move and the arrangement changes, the intensity of light reaching the detector changes.

DLS is popular because it is easy to use, measurements are non-invasive and do not require sample modification, and DLS can provide real-time tracking of changes in hydrodynamic diameters, as well as tracking multiple diffusing species in a solution. However, the efficiency of DLS relies on how well intensity correlation data can be fit to a function. In solutions with single diffusing species, the correlation data can be fitted to an equation using either linearized or power-series approximations. However, when there are multiple species present, inverting a function may prove problematic. There may be many combinations of relaxation that can fit a correlation curve, especially when the constituting relaxation times are close in value. Techniques such as exponent sampling and CONTIN analysis may invert a Laplace transform. However, the inversion of Laplace transforms is mathematically ill conditioned. Small fluctuations in the correlation data that may be produced during experimental measurement can produce large errors in predicted hydrodynamic sizes. Since the entire curve is fitted, uncertainties in the data, particularly at the early or late ends, may produce large errors in the predicted hydrodynamic sizes. When the difference in hydrodynamic sizes is less than 5×, techniques like CONTIN analysis predict a single broad distribution instead of two. It may be advantageous, therefore, to use an alternate approach for robust and high-resolution extraction of relaxation constants in multi-species DLS data. This approach may include sequential extraction of late exponentials (SELE), power series polynomial fitting as an initial guess to least-square minimization fitting, and the use of stretch coefficients.

With respect to SELE, in a multi-species correlation curve, long time-interval data is most likely to contain information on the largest species alone, since contributions from smaller species are likely to have decayed over a long time interval. If only the lag end of the curve is selected to fit an exponential, it is likely that the largest species contribution may be extracted. If the contributed is subtracted from the overall mixture, then the far end of the new correlation curve is likely to have contribution from the second-largest species alone. This may be iteratively repeated to separate the contributions from the species of the mixture.

With respect to power series polynomial fit, the data in a selected window may be fitted to a power series expansion to obtain predicted values for one or more parameters. This may be similar to extracting relaxation times with cumulant analysis. The values extracted from a cumulant-like analysis may form an initial guess for a least-square minimization fit of the entire correlation curve. Not only does this approach give an improved fit of the data, but it may also remove at least a portion of bias resulting from window selection. The may be advantages even in cases where Laplace-transform techniques work well, such as when the exponential decays in the correlation curve are clearly well-separated. For example, the ability to select data windows for exponential fitting may give a better approximation of DLS curves that are not smooth or may have fluctuations. Such DLS curves may tend to reduce the robustness of CONTIN fits. However, the selection window can be simply shifted away from sections of unreliable data.

With respect to stretch coefficients, the variance in species contribution may be captured by using stretch coefficients in SELE. Typical forms of exponential functions used for multi-modal species may not include stretch coefficients or assign a fixed value of 1. By fitting the function with a stretch coefficient, species that are close in size (e.g., <2×) may be treated as a single species but with a spread.

Aspects are described herein with reference to flowchart illustrations and/or block diagrams of methods, apparatus (systems), and computer readable media according to the various embodiments. It will be understood that each block of the flowchart illustrations and/or block diagrams, and combinations of blocks in the flowchart illustrations and/or block diagrams, can be implemented by computer readable program instructions.

The following described exemplary embodiments provide a system, method and computer program that recurrently analyzes mixtures based on subtracting the largest components at steady-state. Referring now to FIG. 1, a functional block diagram of a networked computer environment illustrating a mixture analysis system 100 (hereinafter "system") for analyzing fully-diffused chemical mixtures. It should be appreciated that FIG. 1 provides only an illustration of one implementation and does not imply any limitations with regard to the environments in which different embodiments may be implemented. Many modifications to the depicted environments may be made based on design and implementation requirements.

The system 100 may include a computer 102 and a server computer 114. The computer 102 may communicate with the server computer 114 via a communication network 110 (hereinafter "network"). The computer 102 may include a processor 104 and a software program 108 that is stored on a data storage device 106 and is enabled to interface with a user and communicate with the server computer 114. As will be discussed below with reference to FIG. 4 the computer 102 may include internal components 800A and external components 900A, respectively, and the server computer 114 may include internal components 800B and external components 900B, respectively. The computer 102 may be, for example, a mobile device, a telephone, a personal digital assistant, a netbook, a laptop computer, a tablet computer, a desktop computer, or any type of computing devices capable of running a program, accessing a network, and accessing a database.

The server computer 114 may also operate in a cloud computing service model, such as Software as a Service (SaaS), Platform as a Service (PaaS), or Infrastructure as a Service (IaaS), as discussed below with respect to FIGS. 5 and 6. The server computer 114 may also be located in a cloud computing deployment model, such as a private cloud, community cloud, public cloud, or hybrid cloud.

The server computer 114, which may be used for mixture analysis is enabled to run a Mixture Analysis Program 116 (hereinafter "program") that may interact with a database 112. The Mixture Analysis Program method is explained in more detail below with respect to FIG. 3. In one embodiment, the computer 102 may operate as an input device including a user interface while the program 116 may run primarily on server computer 114. In an alternative embodiment, the program 116 may run primarily on one or more computers 102 while the server computer 114 may be used for processing and storage of data used by the program 116. It should be noted that the program 116 may be a standalone program or may be integrated into a larger mixture analysis program.

It should be noted, however, that processing for the program 116 may, in some instances be shared amongst the computers 102 and the server computers 114 in any ratio. In another embodiment, the program 116 may operate on more than one computer, server computer, or some combination of computers and server computers, for example, a plurality of computers 102 communicating across the network 110 with a single server computer 114. In another embodiment, for example, the program 116 may operate on a plurality of server computers 114 communicating across the network 110 with a plurality of client computers. Alternatively, the program may operate on a network server communicating across the network with a server and a plurality of client computers.

The network 110 may include wired connections, wireless connections, fiber optic connections, or some combination thereof. In general, the network 110 can be any combination of connections and protocols that will support communications between the computer 102 and the server computer 114. The network 110 may include various types of networks, such as, for example, a local area network (LAN), a wide area network (WAN) such as the Internet, a telecommunication network such as the Public Switched Telephone Network (PSTN), a wireless network, a public switched network, a satellite network, a cellular network (e.g., a fifth generation (5G) network, a long-term evolution (LTE) network, a third generation (3G) network, a code division multiple access (CDMA) network, etc.), a public land mobile network (PLMN), a metropolitan area network (MAN), a private network, an ad hoc network, an intranet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of system 100 may perform one or more functions described as being performed by another set of devices of system 100.

Figure 2:
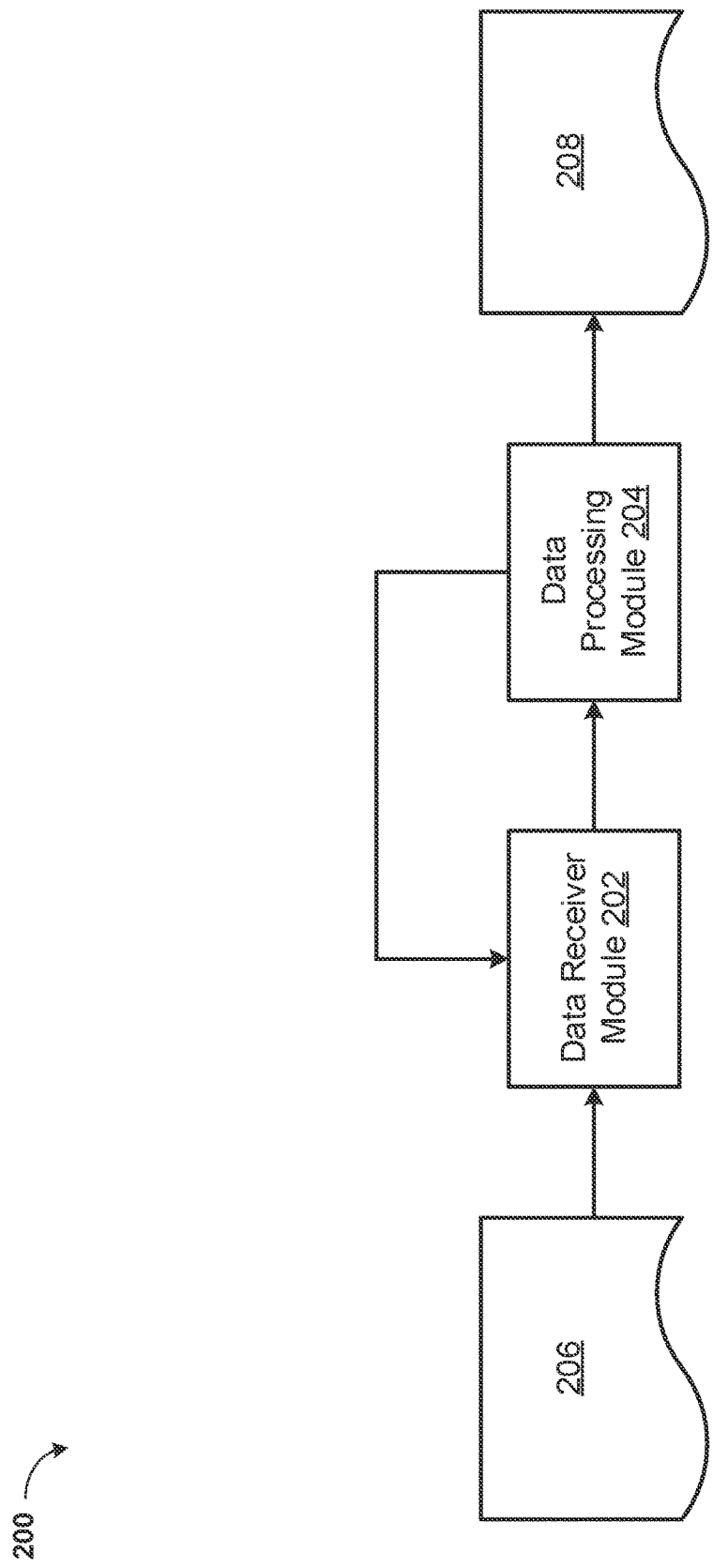
FIG. 2 is a block diagram of a system for mixture analysis, according to at least one embodiment.

Referring now to FIG. 2, an diagram of an exemplary mixture analysis system 200 is depicted. The mixture analysis system 200 may include, among other things, a data receiver module 202 and a data processing module 204. The data receiver module 202 may receive data 206 corresponding to a mixture from an external source via the communication network 110 (FIG. 1). Alternatively, the data receiver module 202 may actively capture data corresponding to a mixture through one or more sensors. The data processing module 204 may determine or receive one or more parameters corresponding to the mixture such as component species within the mixture, decay coefficient, a diffusion coefficient, a relaxation time, and a particle size associated with the one or more component species. The data processing module 204 may iteratively analyze the mixture based on feeding data back to the data receiver module 202 and performing recurrent analysis on the components of the mixture until the mixture is fully analyzed. The data processing module 204 may output data 208, which may include the full analysis results or results of intermediate analysis.

In particle systems where there is no finite memory of past states (i.e., particles are randomly diffusing), the decorrelation of the intensity signal takes the form of a negative exponential function on a logarithmic scale of time intervals $\Delta t$:

$$G(\Delta t)-1=Ae^{-\Gamma \Delta t}$$

where $G(\Delta t)-1$ may be the intensity correlation data as a function of the time interval $\Delta t$. A may be a measure of the scattered light intensity, and $\Gamma$ may be a relaxation constant determining the time-scale over which the particles move and the intensity correlation delays.

When the arrangement of particles changes because of Brownian motion, the relaxation time can be related to a diffusion coefficient D of the scattering species as:

$$\Gamma=Dq^2$$

where q is a scattering vector and a function of the measurement parameters, the scattering wavelength, and the angle.

The Stokes-Einstein relation may be used to relate the diffusion coefficient to the diameter of a freely diffusing bead $d_H$ as:

$$D = \frac{kT}{3\pi\eta d_H}$$

where k may be the Boltzmann constant, T may be the temperature, and $\eta$ may be the viscosity. $d_H$ may be the hydrodynamic diameter (i.e., it may be the diameter of a freely-diffusing bead that has the same diffusion coefficient as the scattering species).

The hydrodynamic diameter may be taken as a measure of particle size and may be the principal quantity measured by DLS. The scatterer in solution may be particles with a spread in size or a polymer with a spread in relaxation modes, each contributing to a relaxation time. The polydispersity or variance in relaxation times may cause the decorrelation of the DLS curves to become gradual or the slope to exponential fall to decrease. The effect may be captured by defining a stretch polynomial $\lambda$ as a measure of polydispersity in the exponential function:

$$G(\Delta t)-1=Ae^{-(\Gamma \Delta t)^\lambda}.$$

When the particle distribution in solution is multimodal (i.e., when there are populations with different sizes or polymers with separated relaxation modes), the DLS correlation curve exhibits multiple decays, each on the time-scale of the contributing size or relaxation mode. In the case of multi-modal solutions, the exponential function can be adapted to represent the sum of contribution from each of the $i^{th}$ diffusing species as:

$$G(\Delta t) - 1 = \sum_{i=1}^{n} A_i e^{-(\Gamma_i \Delta t)^{\lambda_i}}$$

Assume that a correlation data from DLS can be fitted by a sum of contributions from each diffusing species in a mixture. The final correlation curve may be the sum of exponential decays whose exponents may be on the time scale of self-diffusion of the species in the solution. To extract each species contribution to the correlation data, the long-interval time data may include only one exponential. By selecting a window of data toward the end of the correlation curve, the data may be fit to a single exponential. Parameters may be extracted for a single exponential fit before subtracting the long time-interval exponential contribution from the correlation curve.

The long time-interval (i.e., steady-state) data window may be fit in the remnant correlation curve, and the process may be repeated until all relaxation times are sequentially extracted. For example, a sweep of one or more base window sizes associated with the component species may be performed, and a first diffusion coefficient associated with the mixture may be identified. The identified diffusion coefficient may be compared with a second diffusion coefficient corresponding to the species having the largest parameter.

Figure 3:
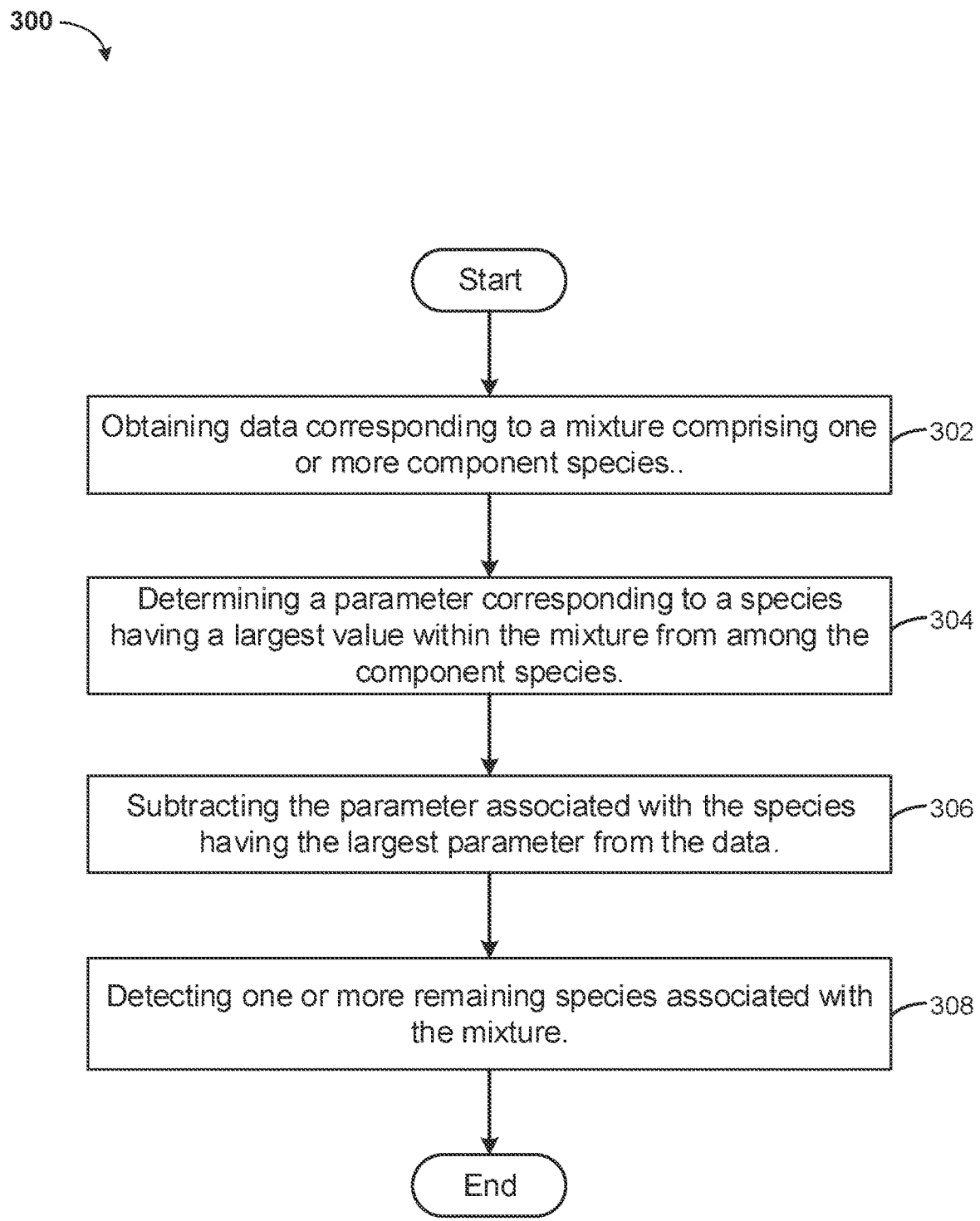
FIG. 3 is an operational flowchart illustrating the steps carried out by a program that analyzes mixtures, according to at least one embodiment.

Referring now to FIG. 3, an operational flowchart illustrating the steps of a method 300 carried out by a program that analyzes chemical mixtures is depicted.

At 302, the method 300 may include obtaining data corresponding to a mixture comprising one or more component species.

At 304, the method 300 may include determining a parameter corresponding to a species having a largest value within the mixture from among the component species.

At 306, the method 300 may include subtracting the parameter associated with the species having the largest parameter from the data.

At 308, the method 300 may include detecting one or more remaining species associated with the mixture.

It may be appreciated that FIG. 3 provides only an illustration of one implementation and does not imply any limitations with regard to how different embodiments may be implemented. Many modifications to the depicted environments may be made based on design and implementation requirements.

Figure 4:
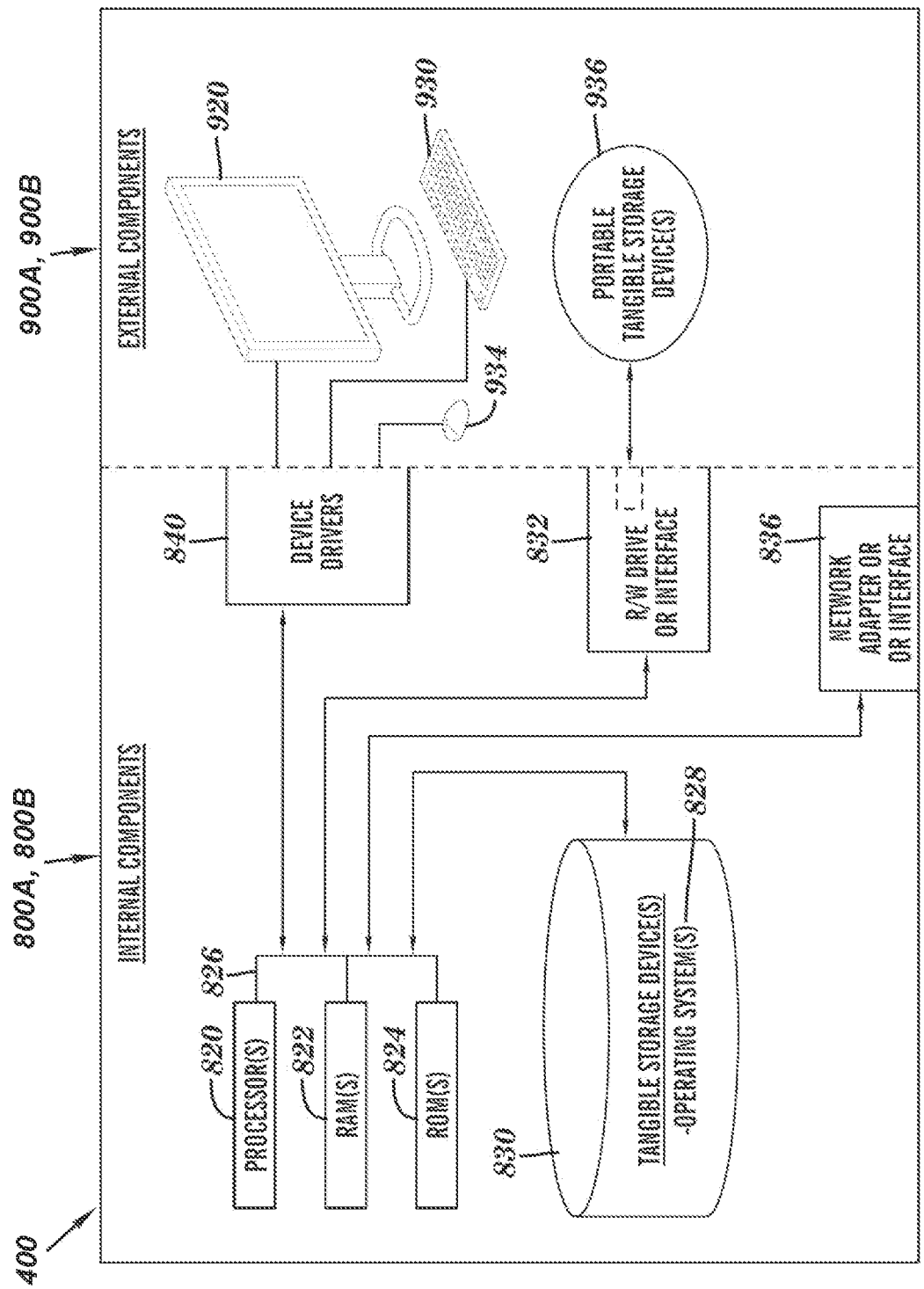
FIG. 4 is a block diagram of internal and external components of computers and servers depicted in FIG. 1 according to at least one embodiment.

FIG. 4 is a block diagram 400 of internal and external components of computers depicted in FIG. 1 in accordance with an illustrative embodiment. It should be appreciated that FIG. 4 provides only an illustration of one implementation and does not imply any limitations with regard to the environments in which different embodiments may be implemented. Many modifications to the depicted environments may be made based on design and implementation requirements.

Figure 5:
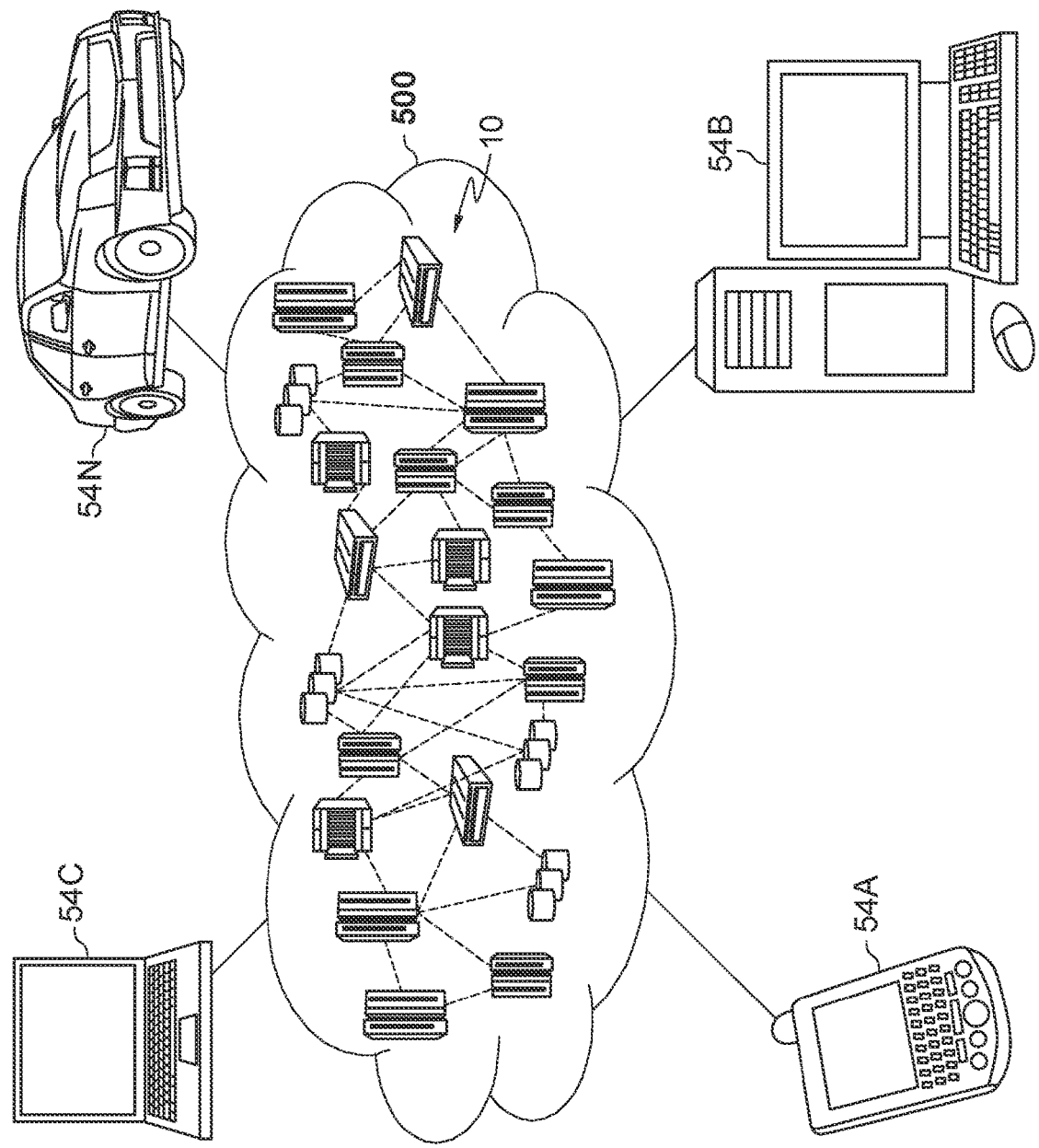
FIG. 5 is a block diagram of an illustrative cloud computing environment including the computer system depicted in FIG. 1, according to at least one embodiment.

Computer 102 (FIG. 1) and server computer 114 (FIG. 1) may include respective sets of internal components 800A,B and external components 900A,B illustrated in FIG. 5. Each of the sets of internal components 800 include one or more processors 820, one or more computer-readable RAMs 822 and one or more computer-readable ROMs 824 on one or more buses 826, one or more operating systems 828, and one or more computer-readable tangible storage devices 830.

Processor 820 is implemented in hardware, firmware, or a combination of hardware and software. Processor 820 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 820 includes one or more processors capable of being programmed to perform a function. Bus 826 includes a component that permits communication among the internal components 800A,B.

The one or more operating systems 828, the software program 108 (FIG. 1) and the Mixture Analysis Program 116 (FIG. 1) on server computer 114 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory, an optical disk, a magneto-optic disk, a solid state disk, a compact disc (CD), a digital versatile disc (DVD), a floppy disk, a cartridge, a magnetic tape, and/or another type of non-transitory computer-readable tangible storage device that can store a computer program and digital information.

Each set of internal components 800A,B also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as the software program 108 (FIG. 1) and the Mixture Analysis Program 116 (FIG. 1) can be stored on one or more of the respective portable computer-readable tangible storage devices 936, read via the respective R/W drive or interface 832 and loaded into the respective hard drive 830.

Each set of internal components 800A,B also includes network adapters or interfaces 836 such as a TCP/IP adapter cards; wireless Wi-Fi interface cards; or 3G, 4G, or 5G wireless interface cards or other wired or wireless communication links. The software program 108 (FIG. 1) and the Mixture Analysis Program 116 (FIG. 1) on the server computer 114 (FIG. 1) can be downloaded to the computer 102 (FIG. 1) and server computer 114 from an external computer via a network (for example, the Internet, a local area network or other, wide area network) and respective network adapters or interfaces 836. From the network adapters or interfaces 836, the software program 108 and the Mixture Analysis Program 116 on the server computer 114 are loaded into the respective hard drive 830. The network may comprise copper wires, optical fibers, wireless transmission, routers, firewalls, switches, gateway computers and/or edge servers.

Each of the sets of external components 900A,B can include a computer display monitor 920, a keyboard 930, and a computer mouse 934. External components 900A,B can also include touch screens, virtual keyboards, touch pads, pointing devices, and other human interface devices. Each of the sets of internal components 800A,B also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, some embodiments are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring to FIG. 5, illustrative cloud computing environment 500 is depicted. As shown, cloud computing environment 500 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Cloud computing nodes 10 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 54A-N shown in FIG. 5 are intended to be illustrative only and that cloud computing nodes 10 and cloud computing environment 500 can communicate with any type of computerized device over any type of network and/or network addressable connection (e.g., using a web browser).

Figure 6:
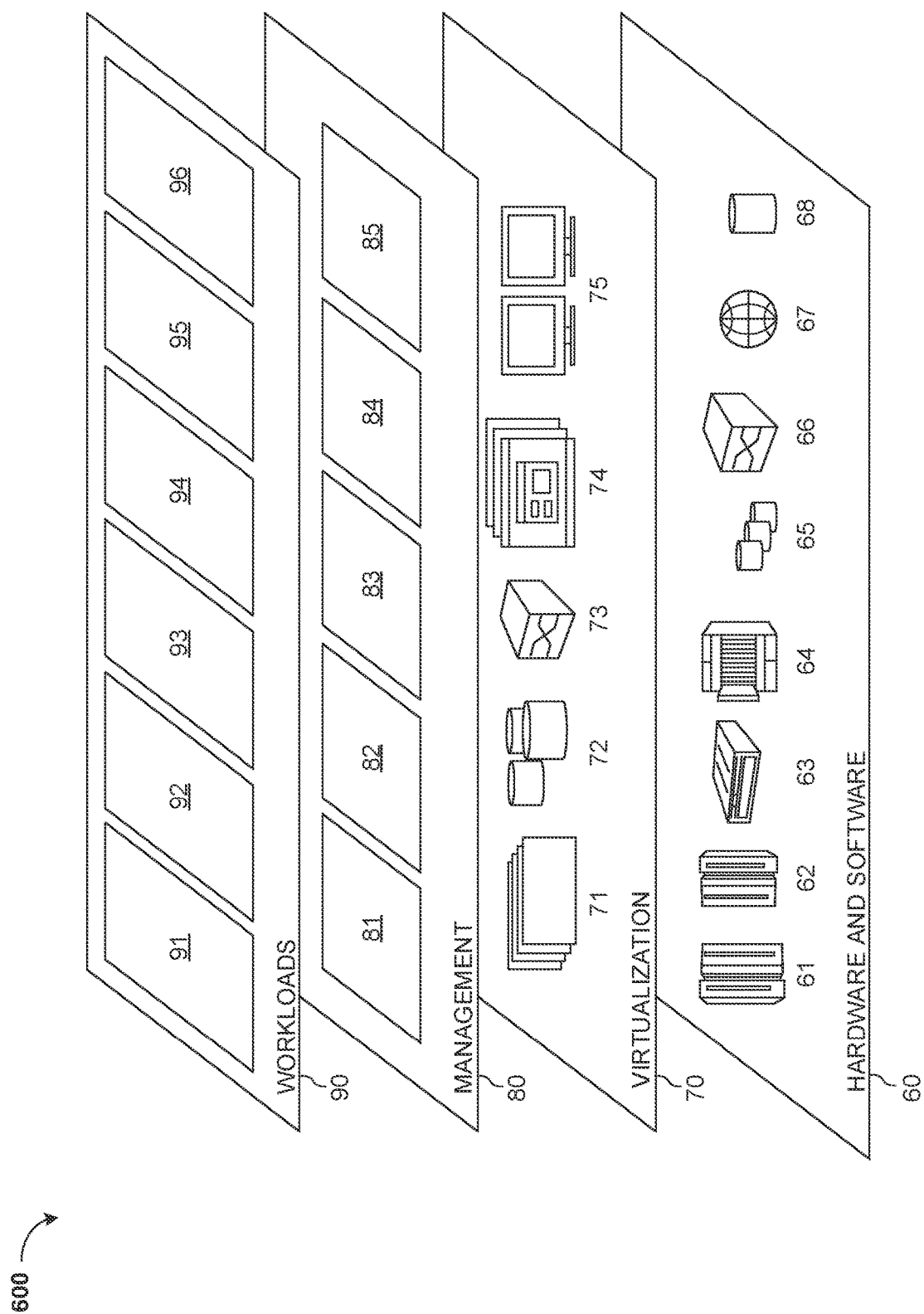
FIG. 6 is a block diagram of functional layers of the illustrative cloud computing environment of FIG. 5, according to at least one embodiment.

Referring to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and Mixture Analysis 96. Mixture Analysis 96 may iteratively subtract data corresponding to the largest component of a mixture.

Some embodiments may relate to a system, a method, and/or a computer readable medium at any possible technical detail level of integration. The computer readable medium may include a computer-readable non-transitory storage medium (or media) having computer readable program instructions thereon for causing a processor to carry out operations.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program code/instructions for carrying out operations may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects or operations.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer readable media according to various embodiments. In this regard, each block in the flowchart or block diagrams may represent a module, segment, or portion of instructions, which comprises one or more executable instructions for implementing the specified logical function(s). The method, computer system, and computer readable medium may include additional blocks, fewer blocks, different blocks, or differently arranged blocks than those depicted in the Figures. In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The descriptions of the various aspects and embodiments have been presented for purposes of illustration, but are not intended to be exhaustive or limited to the embodiments disclosed. Even though combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of analyzing chemical mixtures, executable by a spectrometer, the method comprising:
   obtaining, by the spectrometer, data corresponding to a mixture comprising two or more component species;
   identifying a component species of the two or more component species, wherein identifying the component species comprises determining a parameter having a largest value within the data;
   removing the identified component species from the data, and adding the removed component species to a set of identified component species;
   detecting one or more remaining component species, and adding the one or more detected remaining component species to the set of identified component species, wherein detecting the one or more remaining species comprises:
   performing a sweep of one or more base window sizes associated with the component species;
   identifying a first diffusion coefficient associated with the mixture; and
   comparing the identified first diffusion coefficient with a second diffusion coefficient corresponding to the species having the largest parameter; and
   outputting the set of identified component species from the spectrometer.

2. The method of claim 1, further comprising:
   determining, based on detecting the one or more remaining species, a parameter corresponding to a second species having a largest value within the mixture from among the one or more remaining species;
   subtracting the parameter associated with the second species having the largest concentration from the data; and
   analyzing the parameter corresponding to one or more remaining species associated with the mixture.

3. The method of claim 1, wherein the parameter corresponds to one or more from among a decay coefficient, a diffusion coefficient, a relaxation time, and a particle size associated with the one or more component species.

4. The method of claim 1, wherein parameters corresponding to two species having a similar parameter are subtracted as a single parameter based on fitting the parameter using stretch coefficients.

5. The method of claim 1, wherein the parameter is subtracted based on a least-square minimization fit of the parameter to a power series approximation.

6. The method of claim 1, wherein the parameter associated with the species having the largest concentration is subtracted at steady-state.

7. A spectrometer comprising:
   one or more computer-readable non-transitory storage media configured to store computer program code; and
   one or more computer processors configured to access said computer program code and operate as instructed by said computer program code, said computer program code including:
   obtaining code configured to cause the one or more computer processors to obtain, by the spectrometer, data corresponding to a mixture comprising two or more component species;
   identifying code configured to cause the one or more computer processors to identify a component species of the two or more component species, wherein identifying the component species comprises determining a parameter having a largest value within the data;
   removing code configured to cause the one or more computer processors to remove the identified component species from the data, and adding the removed component species to a set of identified component species;
   detecting code configured to cause the one or more computer processors to detect one or more remaining component species, and adding the one or more detected remaining component species to the set of identified component species, wherein the detecting code comprises:
   performing code configured to cause the one or more computer processors to perform a sweep of one or more base window sizes associated with the component species;

identifying code configured to cause the one or more computer processors to identify a first diffusion coefficient associated with the mixture; and comparing code configured to cause the one or more computer processors to compare the identified first diffusion coefficient with a second diffusion coefficient corresponding to the species having the largest parameter; and outputting code configured to cause the one or more computer processors to output the set of identified component species from the spectrometer.

8. The computer system of claim 7, further comprising:

determining code configured to cause the one or more computer processors to determine, based on detecting the one or more remaining species, a parameter corresponding to a second species having a largest value within the mixture from among the one or more remaining species;

subtracting code configured to cause the one or more computer processors to subtract the parameter associated with the second species having the largest concentration from the data; and analyzing code configured to cause the one or more computer processors to analyze the parameter corresponding to one or more remaining species associated with the mixture.

9. The computer system of claim 7, wherein the parameter corresponds to one or more from among a decay coefficient, a diffusion coefficient, a relaxation time, and a particle size associated with the one or more component species.

10. The computer system of claim 7, wherein parameters corresponding to two species having a similar parameter are subtracted as a single parameter based on fitting the parameter using stretch coefficients.

11. The computer system of claim 7, wherein the parameter is subtracted based on a least-square minimization fit of the parameter to a power series approximation.

12. The computer system of claim 7, wherein the parameter associated with the species having the largest concentration is subtracted at steady-state.

13. A non-transitory computer readable medium having stored thereon a computer program for analyzing chemical mixtures, the computer program configured to cause a spectrometer to:

obtain, by the spectrometer, data corresponding to a mixture comprising two or more component species;

identify a component species of the two or more component species, wherein identifying the component species comprises determining a parameter having a largest value within the data;

remove the identified component species from the data, and add the removed component species to a set of identified component species;

detect one or more remaining component species, and add the one or more detected remaining component species to the set of identified component species wherein detecting the one or more remaining component species comprises to:

perform a sweep of one or more base window sizes associated with the component species;

identify a first diffusion coefficient associated with the mixture; and compare the identified first diffusion coefficient with a second diffusion coefficient corresponding to the species having the largest parameter; and output, from the spectrometer, the set of identified component species.

14. The computer readable medium of claim 13, wherein the computer program is further configured to cause one or more computer processors to:

determine, based on detecting the one or more remaining species, a parameter corresponding to a second species having a largest value within the mixture from among the one or more remaining species;

subtract the parameter associated with the second species having the largest concentration; and analyze the parameter corresponding to one or more remaining species associated with the mixture.

15. The computer readable medium of claim 13, wherein the parameter corresponds to one or more from among a decay coefficient, a diffusion coefficient, a relaxation time, and a particle size associated with the one or more component species.

16. The computer readable medium of claim 13, wherein parameters corresponding to two species having a similar parameter are subtracted as a single parameter based on fitting the parameter using stretch coefficients.

17. The computer readable medium of claim 13, wherein the parameter is subtracted based on a least-square minimization fit of the parameter to a power series approximation.

* * * * *